United States Patent
Miller

(10) Patent No.: US 8,097,749 B2
(45) Date of Patent: Jan. 17, 2012

(54) ISOTHERMAL PROCESS FOR PHOSPHOROMONOCHLORIDITE SYNTHESIS

(75) Inventor: Glenn A. Miller, South Charleston, WV (US)

(73) Assignee: Union Carbide Chemical and Plastics Technology Technology

( * ) Notice: Subject to any disclaimer, the term of this patent is extended or adjusted under 35 U.S.C. 154(b) by 204 days.

(21) Appl. No.: 12/405,335

(22) Filed: Mar. 17, 2009

(65) Prior Publication Data

US 2009/0247790 A1    Oct. 1, 2009

Related U.S. Application Data

(60) Provisional application No. 61/040,304, filed on Mar. 28, 2008.

(51) Int. Cl.
*C07F 9/02* (2006.01)

(52) U.S. Cl. .............. 558/96; 558/73; 558/101; 568/12

(58) Field of Classification Search ........................ None
See application file for complete search history.

(56) References Cited

U.S. PATENT DOCUMENTS

| | | | |
|---|---|---|---|
| 4,769,498 A | 9/1988 | Billig et al. | |
| 4,929,745 A | 5/1990 | Keblys et al. | |
| 5,235,113 A | 8/1993 | Sato et al. | |
| 5,391,799 A * | 2/1995 | Pastor et al. | 558/96 |
| 5,663,369 A | 9/1997 | Kreutzer et al. | |
| 5,688,986 A * | 11/1997 | Tam et al. | 558/338 |
| 6,031,120 A | 2/2000 | Tam | |
| 6,881,867 B2 | 4/2005 | Ahlers et al. | |
| 7,196,230 B2 | 3/2007 | Peng et al. | |
| 7,217,828 B2 * | 5/2007 | Selent et al. | 556/19 |
| 2007/0112219 A1 | 5/2007 | Ortmann et al. | |

FOREIGN PATENT DOCUMENTS

EP    614901    * 9/1994

OTHER PUBLICATIONS

Ahmed et al., Significance of the solubility of hydrogen halides in liquid compounds., Journal of Applied Chemistry vol. 20, Issue 4, Date: Apr. 1970, pp. 109-116.
Barry et al., Triphenylphosphine-Tetrachloromethane Promoted Chlorination and Cyclodehydration of Simple Diols., J. Org. Chem. 1981, 46, 3361-3364.
Buisman et al., Hydridorhodium Diphosphite Catalysts in the Asymmetric Hydroformylation of Styrene., J. Chem. Soc. Dalton Trans. 1995, 409-417.
Cramer et al., Chiral Phosphites and Phosphoramidites Based on the Tropane Skeleton and Their Application in Catalysis., Organometallics 2006, 25, 2284-2291.
Korostylev et al., Chiral pyrophosphites—synthesis and application as ligands in Rh(I)-catalyzed asymmetric hydrogenation., Tetrahedron: Asymmetry 14 (2003) 1905-1909.
Lot et al. New electron-deficient aminophosphonite—phosphite ligands for asymmetric hydroformylation of styrene., Journal of Molecular Catalysis A: Chemical 164 (2000) 125-130.

* cited by examiner

*Primary Examiner* — Sudhakar Katakam

(57) ABSTRACT

The present invention relates to a process for preparation of a phosphoromonochloridite in high yield by contacting phosphorus trichloride ($PCl_3$) with an aromatic diol in a solution of one or more organic solvents under reaction conditions sufficient to produce the phosphoromonochloridite. The reaction is carried out by adding a feed solution containing the aromatic diol dissolved in a first organic solvent into a reaction zone containing $PCl_3$, and optionally one or more second organic solvents, the addition being conducted so as to maintain substantially isothermal process conditions. The reaction solution comprises greater than 0.01 to less than 5 mole percent of a nitrogen base.

20 Claims, No Drawings

ISOTHERMAL PROCESS FOR PHOSPHOROMONOCHLORIDITE SYNTHESIS

CROSS-REFERENCE TO PRIOR APPLICATION

This application claims the benefit of U.S. Provisional Application No. 61/040,304 filed Mar. 28, 2008.

FIELD OF THE INVENTION

This invention relates generally to a process for preparation of phosphoromonochloridites, which are intermediates for synthesis of organopolyphosphites.

BACKGROUND

Phosphites represent a diverse class of organic phosphorus compounds that are useful as ligands for homogeneous catalysis and as components of plasticizers, flame retardants, UV stabilizers and antioxidants. Phosphites can be further classified as organomonophosphites and organopolyphosphites. Organopolyphosphites are particularly useful for certain homogeneous catalysis; for example, U.S. Pat. No. 4,769,498 generally relates to synthesis of organopolyphosphites and use thereof as ligands in hydroformylation processes.

Phosphoromonochloridites are intermediates for synthesizing organopolyphosphites; see, for example, U.S. Pat. Nos. 6,031,120; 5,663,369, and 4,769,498. A phosphoromonochloridite is typically synthesized in a condensation reaction by contacting phosphorus trichloride ($PCl_3$) with one molar equivalent of a di-alcohol or two molar equivalents of a mono-alcohol under reaction conditions dependent upon the reactivity of the starting alcohol and the resulting phosphoromonochloridite. For each molecule of a phosphoromonochloridite produced, the condensation reaction produces two molecules of hydrogen chloride (HCl). In order for the condensation reaction to achieve high, for example, greater than 90 percent, conversion of the alcohol, HCl needs be removed from the reaction solution.

One approach for HCl removal from the condensation reaction is to neutralize HCl using a nitrogen base, in an amount stoichiometric to or in excess to the theoretical amount of HCl to be produced. See, for example, U.S. Pat. Nos. 5,235,113; 6,031,120, and 7,196,230, U.S. patent application publication 2007/0112219 A1, and *Journal of Molecular Catalysis* A: Chemical 164 (2000) 125-130. When a nitrogen base is used, however, the resulting nitrogen base-HCl salt must be removed from the reaction mixture by a filtration procedure, which generates chloride and nitrogen-containing wastes that, in turn, increase cost.

Another approach for HCl removal from the $PCl_3$-alcohol condensation reaction involves heating a mixture of the alcohol and a large excess amount of the $PCl_3$ at a temperature sufficiently high to reflux $PCl_3$ (boiling point (bp): 74-78° C.), which drives off the HCl. A nitrogen base is not needed in this approach. For example, U.S. Pat. No. 4,769,498 discloses a procedure for producing 1,1'-biphenyl-2,2'-diyl phosphoromonochloridite by refluxing a mixture of 2,2'-biphenol with 3.7 molar equivalents (2.7 equivalents in excess) of $PCl_3$. The product, 1,1'-biphenyl-2,2'-diyl phosphoromonochloridite, is disclosed to be isolated in 72 mole percent yield, based on moles of 2,2'-biphenol used, by distillation under reduced pressure. Another procedure, as referenced in Korostyler et al., *Tetrahedron: Asymmetry*, 14 (2003) 1905-1909, and Cramer et al., *Organometallics*, Vol. 25, No. 9 (2006) 2284-2291, synthesizes 4-chlorodinaphtho[2,1-d:1',2'-f][1,3,2]dioxaphosphepine by heating a mixture of 1,1'-bi-2-naphthol and 11.5 molar equivalents of $PCl_3$ at 75-80° C. One undesirable feature of the aforementioned approach is that it involves the need to remove and handle a large excess amount of $PCl_3$, which reacts exothermically with moisture and typically involves additional safety considerations. It would be desirable to reduce the excess amount of $PCl_3$ to be used in the process.

In view of the above, there is a need in the art for a more efficient process for producing phosphoromonochloridites.

SUMMARY OF THE INVENTION

The present invention provides for a novel synthetic process for preparing a phosphoromonochloridite comprising contacting an aromatic diol represented by formula I:

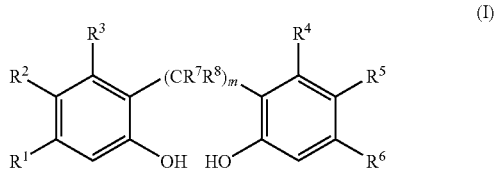

(I)

wherein:
m is zero, 1 or 2;
$R^1$, $R^2$, $R^3$, $R^4$, $R^5$, $R^6$, $R^7$ and $R^8$ are each independently selected from hydrogen, halogen, and monovalent $C_1$-$C_{10}$ substituted or unsubstituted hydrocarbyl moieties;
and wherein optionally, $R^2$ can be bonded to $R^3$ to form a substituted or unsubstituted hydrocarbylene moiety so as to form a 5- or 6-membered ring; and/or
optionally, $R^4$ can be bonded to $R^5$ to form a substituted or unsubstituted hydrocarbylene moiety so as to form a 5- or 6-membered ring.
with phosphorus trichloride ($PCl_3$) in a reaction solution in a reaction zone, which reaction solution comprises greater than about 0.01 and less than 5 mole percent of a nitrogen base, calculated on moles of aromatic diol, at a temperature sufficient to produce a phosphoromonochloridite represented by formula II:

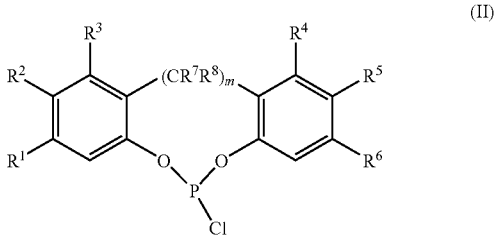

(II)

wherein m and $R^1$ through $R^8$ have the definitions given hereinabove, and sufficient to drive off HCl produced during reaction; wherein the contacting is carried out by adding a feed solution of the aromatic diol to the reaction zone comprising $PCl_3$ to form the reaction solution, the addition being at such a rate that reaction temperature remains substantially isothermal, the feed solution comprising essentially all of the aromatic diol dissolved in a first organic solvent.

DETAILED DESCRIPTION OF THE INVENTION

The process of the invention, which hereinafter is referred to simply as "the process," employs an aromatic diol, phosphorus trichloride (PCl₃), and a first organic solvent to dissolve the aromatic diol to make a feed solution. Preferably, the process employs also a second organic solvent to dilute the PCl₃.

In describing the present invention, certain phrases, terms, and words are used that are defined herein. When interpreting a meaning of a phrase, term, or word, its definition here governs unless, for a particular use, a different meaning is stated elsewhere in this specification or unless a context of the use of the phrase, term, or word clearly indicates a different meaning is intended from the definitions provided here.

The articles "a" and "the" refer to singular and plural forms of what is being modified by the articles. When used in front of a first member of a list of two or more members, the words "a" and "the" independently refer to each member in the list. As used herein, "a," "an," "the," "at least one," and "one or more" are used interchangeably. The term "comprises" and variations thereof do not have a limiting meaning where these terms appear in the description and claims. Thus, for example, a reactant mixture that comprises "an" aromatic diol can be interpreted to mean that the aromatic diol includes "one or more" aromatic diols. The term "or" refers to members in a list either singly or in any combination.

A "nitrogen base" is defined as a nitrogen-containing organic compound that is capable of neutralizing HCl to form a salt that is essentially insoluble in an organic solvent employed in the process.

The term "organic solvent" has its ordinary meaning referring to a substance that is a liquid at ambient temperature and pressure and is capable of dissolving another substance (solute) to form a uniformly dispersed mixture (solution) at the molecular or ionic level.

For the purposes of this invention, the term "ambient temperature" is taken as 22° C.±2° C.

The term "aprotic" refers to an organic solvent that does not donate a proton.

A "polar aprotic organic solvent" is defined as an aprotic organic solvent having a dielectric constant of greater than about 6 and is not a nitrogen base as defined above.

A "hydrocarbyl" moiety is defined as a monovalent moiety derived from a hydrocarbon by removal of one hydrogen atom from one carbon atom.

A "hydrocarbylene" moiety is defined as a divalent moiety derived from a hydrocarbon by removal of two hydrogen atoms from two carbon atoms.

A "substituted hydrocarbyl" or "substituted hydrocarbylene" moiety means that one or more H or C atoms in the hydrocarbyl or the hydrocarbylene is substituted by one or more heteroatoms or one or more functional groups that contain one or more heteroatoms, which include, but are not limited to, nitrogen, oxygen, sulfur, phosphorus, boron, chlorine, bromine, and iodine. A substituted hydrocarbyl moiety can be a "hydrocarbyloxy" moiety, which has a generic formula of RO—, wherein R is a hydrocarbyl or substituted hydrocarbyl moiety as defined above.

Referring to an organic solvent, the term "boiling point" is defined as the temperature of a liquid at which its vapor pressure is essentially equal to a defined pressure of 1 atmosphere (101 kPa).

The process employs an aromatic diol represented by formula I:

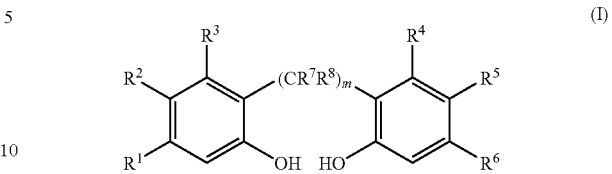

wherein m, $R^1$, $R^2$, $R^3$, $R^4$, $R^5$, $R^6$, $R^7$ and $R^8$ are as defined in the Summary of the Invention. Preferably, m is zero or 1, and $R^7$ and $R^8$ are each hydrogen. More preferably, m is zero or 1, and $R^1$, $R^6$, $R^7$ and $R^8$ are each hydrogen.

Examples of aromatic diols that can be employed in the process include, but are not limited to, 2,2'-biphenol, 5,5'-dimethyl-2,2'-biphenol, 5,5'-dichloro-2,2'-biphenol, 5,5'-dibromo-2,2'-biphenol, 5,5'-diiodo-2,2'-biphenol, 5,5'-diethyl-2,2'-biphenol, 5,5'-di-n-propyl-2,2'-biphenol, 5,5'-di-isopropyl-2,2'-biphenol, 5,5'-di-n-butyl-2,2'-biphenol, 5,5'-di-sec-butyl-2,2'-biphenol, 5,5'-di-iso-butyl-2,2'-biphenol, 5,5'-di-tert-butyl-2,2'-biphenol, 5,5'-di-n-amyl-2,2'-biphenol, 5,5'-bis(1,1-dimethylpropyl)-2,2'-biphenol, 5,5'-bis(2,2-dimethylpropyl)-2,2'-biphenol, 5,5'-di-n-hexyl-2,2'-biphenol, 5,5'-di-2-hexyl-2,2'-biphenol, 5,5'-di-3-hexyl-2,2'-biphenol, 5,5'-di-n-heptyl-2,2'-biphenol, 5,5'-di-2-heptyl-2,2'-biphenol, 5,5'-di-3-heptyl-2,2'-biphenol, 5,5'-di-4-heptyl-2,2'-biphenol, 5,5'-di-n-octyl-2,2'-biphenol, 5,5'-di-2-octyl-2,2'-biphenol, 5,5'-di-3-octyl-2,2'-biphenol, 5,5'-di-4-octyl-2,2'-biphenol, 5,5'-bis(1,1,3,3-tetramethylbutyl)-2,2'-biphenol, 5,5',6,6'-tetramethyl-2,2'-biphenol, 5,5'-diphenyl-2,2'-biphenol, 5,5'-bis(2,4,6,-trimethylphenyl)-2,2'-biphenol, 5,5'-dimethoxy-2,2'-biphenol, 5,5'-diethoxy-2,2'-biphenol, 5,5'-di-n-propoxy-2,2'-biphenol, 5,5'-di-isopropoxy-2,2'-biphenol, 5,5'-di-n-butoxy-2,2'-biphenol, 5,5'-di-sec-butoxy-2,2'-biphenol, 5,5'-di-iso-butoxy-2,2'-biphenol, 5,5'-di-tert-butoxy-2,2'-biphenol, 1,1'-bi-2-naphthol, bis(2-hydroxyphenyl)methane, 2,2'-methylenebis(4-chlorophenol), and 2,2'-methylenebis(4-tert-butyl-phenol). One preferred aromatic diol is 2,2'-biphenol.

Phosphorus trichloride, as may be obtained from any commercial supplier, is also required for the process of this invention. On one hand, a low excess molar amount of PCl₃ to moles of aromatic diol used (e.g., molar ratio greater than 1.0/1 to 3.5/1) is desirably employed in the process, because the lower excess reduces the amount of unconverted PCl₃ to be removed from the condensation reaction solution to obtain a phosphoromonochloridite product solution. On the other hand, a high excess molar amount of PCl₃ to moles of the aromatic diol used (e.g., molar ratio greater than 4/1) is desirably employed in the condensation reaction solution to minimize side reactions of the aromatic diol with the phosphoromonochloridite. For example, 2,2'-biphenol can react with its reaction product, 1,1'-biphenyl-2,2'-diyl phosphoromonochloridite, to produce, 2'-(dibenzo[d,f][1,3,2]dioxaphosphepin-6-yloxy)biphenyl-2-ol (formula III) and 2,2'-bis(dibenzo[d,f][1,3,2]dioxaphosphepin-6-yloxy)biphenyl (formula IV).

Formula III

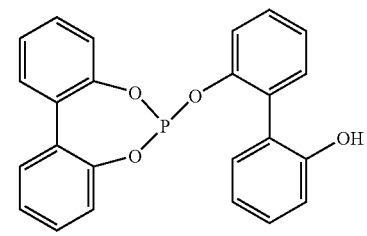

Formula IV

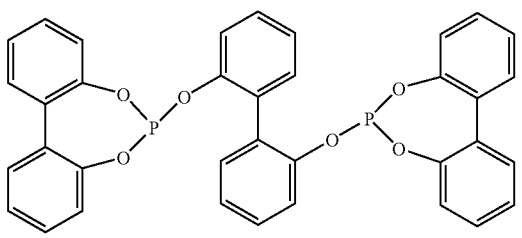

These byproduct reactions are desirably avoided.

In the present invention the advantages of both higher and lower excess amounts of PCl₃ relative to aromatic diol used can be simultaneously achieved, when the aromatic diol is dissolved in a feed solution and the feed solution is added into the reaction zone in a controlled rate, such that essentially no aromatic diol accumulates in the resulting reaction solution. Under these conditions, the rate of the condensation reaction substantially matches or is faster than the rate of addition of the aromatic diol. Accordingly, the molar ratio of PCl₃ to aromatic diol dissolved in the reaction solution is much higher than the molar ratio of PCl₃ to total aromatic diol employed in the process, thereby resulting in fewer side reactions. For illustrative purposes, while the molar ratio of PCl₃ to moles of total aromatic diol used may be only 2.5/1, the molar ratio of PCl₃ to moles of aromatic diol dissolved in the reaction solution at any given time may be greater than 10/1, and upwards of 50/1 or higher. Thus, in accordance with this invention, provided that some excess PCl₃ is employed in this process, the molar ratio of PCl₃ to total aromatic diol may be desirably reduced, as compared with prior art processes, thereby relieving to some extent the problem of removing even larger quantities of PCl₃ when the process is complete.

Accordingly, the molar ratio of PCl₃ to total aromatic diol employed in the process advantageously is greater than about 1.0, preferably greater than about 1.1, and more preferably greater than about 1.2. The molar ratio of PCl₃ to total aromatic diol employed in the process advantageously is less than 3.5, preferably less than 3.3, more preferably less than 3.1, still more preferably less than about 2.9, still more preferably less than about 2.7, still more preferably less than about 2.5, still more preferably less than about 2.3, still more preferably less than about 2.1, and still more preferably less than about 1.9.

The desired functions of the first organic solvent in the process include, but are not limited to a) dissolving and diluting the aromatic diol to produce a feed solution, and optionally b) solubilizing the reaction product, a phosphoromonochloridite of formula II.

To perform at least one of the above-described functions, the first organic solvent for the process is selected from solvents capable of dissolving the aromatic diol substantially completely to obtain a feed solution. Solvents that are suitably employed as the first organic solvent are described hereinafter. The concentration of the aromatic diol by weight, based on the weight of the feed solution, advantageously is greater than about 5 percent, preferably greater than about 10 percent and more preferably greater than about 15 percent. The concentration of the aromatic diol by weight, based on the weight of the feed solution, advantageously is less than about 50 percent, preferably less than about 45 percent, and more preferably less than about 40 percent. These concentration ranges are applicable in each embodiment of the process described hereinbelow unless otherwise stated. Depending on the solubility of the aromatic diol in the first organic solvent, the feed solution can be prepared at ambient temperature or at an elevated temperature to obtain a concentration of the aromatic diol within the above-mentioned ranges.

The solubility of the aromatic diol in the organic solvent can be measured by using known procedures. For example, the solubility of the aromatic diol in the organic solvent at a specific temperature can be determined by an equilibrium solubility method, which employs a saturated solution of the aromatic diol, obtained by stirring an excess amount of the aromatic diol in the organic solvent at the specific temperature for a sufficient period of time until equilibrium is achieved. Thereafter, the resulting liquid phase saturated solution, the resulting solid phase, or both liquid and solid phases are analyzed by any conventional analytical method to arrive at the solubility of the aromatic diol in the organic solvent.

The feed solution is added into a reaction zone advantageously containing neat PCl₃, preferably containing PCl₃ and a second organic solvent. The desirable functions of the second organic solvent, if employed in the process, include, but are not limited to a) further minimizing production of by-products by diluting both the PCl₃ employed and the phosphoromonochloridite produced in the process, b) dissipating heat from the condensation reaction, c) facilitating evolution of HCl from the condensation reaction solution, d) enabling efficient agitation, especially, early in the process, and e) simplifying isolation of the phosphoromonochloridite as a solution in the second organic solvent by removal of any excess amount of PCl₃ and a portion or all of the first organic solvent. To perform at least one of the above described functions, the second organic solvent for the process advantageously is selected from conventional hydrocarbon solvents and chlorinated hydrocarbon solvents. Preferably, the second organic solvent has a boiling point above about 90° C., more preferably above about 95° C., and still more preferably above about 100° C., but typically lower than about 250° C., so that any excess PCl₃ used in the process can be preferentially removed from the reaction solution, e.g. via distillation, to obtain a product solution comprising the phosphoromonochloridite. More preferably, the second organic solvent is stable (i.e., non-reactive) to HCl and has a low HCl solubility, which is defined as less than about 0.2 moles of HCl per mole of solvent at 20° C. and a total pressure of 760 mm Hg (101 kPa).

Procedures for determining HCl solubility in an organic solvent are well known. For example, bubbler procedures were used by Gerrard et al. (*Chem. Rev.,* 1959, 59, 1105) and Ahmed et al. (*J. Appl. Chem.,* 1970, Vol. 20, April, page 109-116.) for measuring HCl solubility in many organic solvents. Examples of HCl solubility in organic solvents reported by Gerrard et al. and Ahmed et al. are shown in Table 1.

TABLE 1

HCl solubility in organic solvents at
a total pressure of 760 mm Hg (101 kPa)

| Organic solvent | HCl solubility Mol/mol organic solvent | |
|---|---|---|
| | At 10° C. | At 20° C. |
| n-Heptane | 0.02 | 0.015 |
| n-Decane | 0.028 | — |
| Benzene | 0.053 | 0.047 |
| Toluene | 0.07 | 0.051 |
| m-Xylene | 0.08 | 0.071 |
| o-Xylene | 0.08 | 0.061 |
| p-Xylene | 0.08 | 0.064 |
| Chlorobenzene | — | 0.033 |
| Tetrahydrofuran | 1.38 | — |

Toluene, chlorobenzene, o-xylene, m-xylene, p-xylene, ethylbenzene, heptane, octane, and mixtures thereof are non-limiting examples of organic solvents that can be selected as the second organic solvent.

The volume of the second organic solvent, when employed, advantageously is greater than about one time, preferably greater than about 2 times, more preferably greater than about 3 times the volume of the PCl$_3$. The volume of the second organic solvent, when employed, advantageously is less than about 15 times, preferably less than about 13 times, more preferably less than about 11 times the volume of the PCl$_3$. These volume ranges of the second organic solvent, when employed, are applicable to each embodiment described hereinbelow unless otherwise stated.

The reaction zone advantageously comprises a reactor equipped with a reflux condenser, the top of which is purged with a stream of an inert gas, such as nitrogen, which then passes through an attached sodium hydroxide (NaOH) scrubber. The reactor advantageously is equipped with a means for efficient agitation, such as a mechanical stirrer. The PCl$_3$, preferably provided in a solution of PCl$_3$ in the second organic solvent, advantageously is heated in the reactor to a desired reaction temperature and maintained thereat as the feed solution containing the aromatic diol is added. The reaction temperature advantageously is sufficient to produce the phosphoromonochloridite and sufficient to drive off the condensation co-product, hydrogen chloride (HCl), which is removed from the reactor through the condenser and trapped in the sodium hydroxide scrubber. The reaction temperature advantageously is greater than about 40° C., preferably greater than about 45° C., and more preferably greater than about 50° C., and advantageously is below about 115° C., preferably below about 110° C., and more preferably below about 105° C. These temperature ranges are applicable in each embodiment described hereinbelow unless otherwise stated.

Addition of the feed solution into the reaction zone advantageously is carried out at a rate such that the reaction temperature remains substantially isothermal during the course of the addition. The term "substantially isothermal" means that the temperature is maintained at a selected reaction temperature ("target temperature") within ±5° C., the target temperature lying within the ranges mentioned hereinbefore. The temperature of the reaction solution is measured with any conventional temperature sensing means, including a temperature probe, such as a calibrated thermocouple, located within the reaction solution.

Generally, the process is carried out at ambient pressure, taken as about 1 atmosphere (101 kPa), but higher or lower pressures may be employed, if desired. Preferably, the reaction is conducted under a blanket of inert atmosphere, such as nitrogen, argon, or helium.

The addition of the feed solution to the reaction zone is completed advantageously in more than about 3 hours, preferably in more than about 4 hours, more preferably in more than about 5 hours, and advantageously in less than about 60 hours, preferably in less than about 55 hours, and more preferably in less than about 50 hours. These time ranges are applicable in each embodiment described hereinbelow for completing addition of a feed solution, unless otherwise stated.

After completion of the feed solution addition, the reaction solution advantageously is agitated for an additional period of time until substantially all of the aromatic diol is converted in the reaction. The additional period of time advantageously is less than about 5 hours, preferably less than about 4 hours, and more preferably less than about 3 hours, but typically more than about 30 minutes. Progress of the condensation reaction can be conveniently monitored by taking aliquots of the reaction solution for $^1$H, $^{13}$C, and/or $^{31}$P nuclear magnetic resonance analysis (NMR) (disappearance of PCl$_3$ and/or the aromatic diol, and/or appearance of the phosphoromonochloridite). The quantity of HCl produced as a co-product of the process can be measured by analyzing the effluent stream from the reaction zone. Conventional analysis methods may be employed including (a) titration of the scrubber solution; (b) use of a weigh cell; and (c) measurement of the heat of neutralization in the scrubber by use of a temperature sensing means, such as, a thermocouple.

In a first embodiment of the process, the first organic solvent advantageously is selected from hydrocarbon solvents and chlorinated hydrocarbon solvents identical to those described hereinabove in connection with the second organic solvent. Accordingly, in this first embodiment, the first organic solvent has a boiling point preferably above about 90° C., more preferably above about 95° C., and still more preferably above about 100° C., but typically less than about 250° C., so that any excess PCl$_3$ used in the process can be preferentially removed from the reaction solution to obtain a product solution comprising the phosphoromonochloridite. If desired, this embodiment of the process can be carried out without employing the second organic solvent. Preferably, however, the process employs the second organic solvent, which can be a different hydrocarbon or chlorinated hydrocarbon solvent from the first organic solvent, or preferably, is the same as the first organic solvent.

In this first embodiment, generally, the aromatic diol has a low solubility in the first organic solvent. For example, 2,2'-biphenol has a solubility in toluene of about 2.7 percent and 7.3 percent by weight, based on the weight of the solution at 19° C. and 40° C., respectively. Accordingly, this embodiment generally requires a) a large quantity of the first organic solvent to solubilize essentially all of the aromatic diol, and/or b) preparation and maintenance of the feed solution at an elevated temperature to increase and maintain solubility of the diol in the feed solution. Accordingly, the feed solution, preferentially comprising toluene and 2,2'-biphenol, is prepared at a temperature advantageously greater than about 40° C., preferably greater than about 45° C., and more preferably greater than about 50° C., and advantageously below about 80° C., preferably below about 75° C., and more preferably below about 70° C. Advantageously, the feed solution temperature is lower than the reaction temperature of the process. In this embodiment, however, the feed solution is advantageously kept at a temperature substantially the same as or slightly higher than the temperature at which it is prepared to prevent precipitation of the aromatic diol. Preferably, the feed solution is used immediately after it is prepared. A means for maintaining the temperature of the feed solution is also necessary during the addition of the feed solution into the reaction zone to prevent precipitation of the aromatic diol in the feed pipes. Precipitation in the feed pipes can cause operational problems. Any means known in the art for maintaining elevated temperatures of feed pipes can be employed, such as using insulated and heated pipes.

The amount of the first organic solvent to be employed in this embodiment of the process depends on the solubility of the aromatic diol at the temperature at which the feed solution is prepared and depends on the desired concentration of the aromatic diol in the feed solution. Any amount of first organic solvent can be employed so long as the amount is sufficient to dissolve essentially all of the aromatic diol to make the feed solution having the desired concentration of the aromatic diol within the ranges described hereinabove. The term "essentially all" means that greater than about 98 weight percent, preferably, greater than 99 weight percent, and more preferably, 100 percent of the aromatic diol is dissolved in the first organic solvent. Generally, the phosphoromonochloridite of formula II is more soluble in the first organic solvent than its starting aromatic diol. Therefore, the amount of the first organic solvent employed to prepare the feed solution advantageously is sufficient to solubilize the phosphoromonochloridite produced in the process at the reaction temperature employed.

In this first embodiment of the process, both the first organic solvent and the second organic solvent, if employed, have low HCl solubility and are stable to HCl, as noted hereinabove. The process can advantageously be carried out at a reaction temperature either sufficiently high to reflux the reaction solution or below the reflux temperature of the reaction solution, as desired. The reaction temperature and the rate of feed solution addition advantageously are such that the temperature of the reaction remains substantially isothermal, as noted hereinbefore. When these conditions are met, then essentially no aromatic diol should accumulate in the reaction solution, and the rate of HCl evolution should be controlled within the capacity of the sodium hydroxide scrubber so as to avoid pressure buildup and excess heat generation in the scrubber.

In a second embodiment of the process, the first organic solvent advantageously is selected from polar aprotic organic solvents that have a dielectric constant (DC) of greater than about 6. Additionally, the polar aprotic organic solvent should be capable of solubilizing essentially all of the aromatic diol at about ambient temperature in a feed solution having a concentration of the aromatic diol within the ranges described hereinabove. The term "essentially all" means that greater than about 98 weight percent, preferably, greater than 99 weight percent, and more preferably, 100 percent of the aromatic diol is dissolved in the first organic solvent. The second organic solvent, described hereinabove, advantageously is employed in this embodiment of the process.

Preferably, the polar aprotic organic solvent is miscible with the second organic solvent and has a boiling point (bp) lower than that of the second organic solvent. More preferably, the boiling point of the polar aprotic organic solvent is more than 10° C. lower than that of the second organic solvent, so that the polar aprotic organic solvent can be removed preferentially from the reaction product solution. Still more preferably, the boiling point of the polar aprotic organic solvent is at least 10° C. lower than the boiling point of $PCl_3$. Tetrahydrofuran (THF, DC: 7.1@20° C.), dichloromethane (DC: 9.1@20° C.) and dichloroethane (DC: 10.7@25° C.) are non-limiting examples of polar aprotic organic solvents that can be used as the first organic solvent. THF is a more preferred first organic solvent.

In this second embodiment, the reaction temperature advantageously is sufficient to reflux the reaction solution containing the first and the second organic solvents. The reaction temperature is selected from the ranges described hereinabove. Addition of the feed solution into the reaction zone advantageously is carried out at a rate such that the reaction temperature remains substantially isothermal to maintain a reflux of the reaction solution during the course of the addition. At such a reflux temperature, the condensation reaction is fast and the reflux drives off HCl quickly from the solution phase, so that the HCl evolution rate is controlled by the rate of feed solution addition. The rate of HCl evolution advantageously is controlled to be within the capacity of the sodium hydroxide scrubber being employed to avoid pressure buildup and excess heat generation in the scrubber.

In a third embodiment of the process, the condensation reaction is carried out with a first organic solvent comprising a mixture of solvents, while the second organic solvent may or may not be employed. Preferably, the second organic solvent is employed. The first organic solvent advantageously comprises a mixture of a polar aprotic organic solvent, such as any of those described hereinbefore, and a hydrocarbon solvent or chlorinated hydrocarbon solvent, such as any of those described hereinbefore. The preferred polar aprotic organic solvent is THF. The amounts of the polar aprotic organic solvent and the hydrocarbon or chlorinated hydrocarbon solvent to be employed in this third embodiment of the process are sufficient to dissolve essentially all the aromatic diol at ambient temperature to make a feed solution having a concentration within the ranges described hereinabove. In this context, the term "essentially all" means again that greater than about 98 weight percent, preferably, greater than 99 weight percent, and more preferably, 100 percent of the aromatic diol is dissolved in the first organic solvent. Any weight ratio of the polar aprotic organic solvent to the hydrocarbon or chlorinated hydrocarbon solvent is suitably employed, so long as the solvent mixture is capable of solubilizing the aromatic diol essentially completely at ambient temperature. The weight ratio of the polar aprotic organic solvent to the hydrocarbon solvent or chlorinated hydrocarbon solvent advantageously is greater than about 1/10, preferably, greater than about 1/5, and is advantageously less than about 10/1, preferably, less than about 5/1. When the second organic solvent is not employed in the process, the amount of the hydrocarbon or chlorinated hydrocarbon solvent employed in the feed mixture is sufficient to solubilize the phosphoromonochloridite product after the polar aprotic organic solvent and excess $PCl_3$ are removed from the reaction solution. Preferably, when a second organic solvent is employed in the process, the total amount of the hydrocarbon or chlorinated hydrocarbon solvent employed, both as the second organic solvent and in the mixture of the first organic solvent, is sufficient to solubilize the reaction product after the polar aprotic organic solvent and the excess $PCl_3$ are removed from the reaction solution.

As the first organic solvent, or portion thereof, tetrahydrofuran has many desirable properties, including the boiling point thereof and the beneficial solubility of aromatic diols therein. Employing a mixture of THF and a hydrocarbon or chlorinated hydrocarbon solvent as the first organic solvent advantageously reduces the amount of hydrocarbon or chlorinated hydrocarbon solvent necessary to solubilize essentially all the aromatic diol at ambient temperature to form the feed solution. One mole of tetrahydrofuran, however, is capable of absorbing/dissolving 1.38 moles of hydrogen chloride at 10° C. and a total pressure of 760 mm Hg (101 kPa). The solubility of HCl is lower at a higher temperature. Tetrahydrofuran may also react with HCl to produce 4-chlorobutanol under certain conditions, such as high concentration of HCl and high temperatures; see, for example, Barry et al., *Journal of Organic Chemistry* (1981), 46(16), 3361-4. Consequently, it is beneficial to keep the quantity of THF in the feed solution as low as necessary to solubilize the aromatic diol, so as to reduce the concentration of HCl in the reaction solution and minimize any potential reaction between THF and HCl.

In the third embodiment of the process, the $PCl_3$, preferably the solution of $PCl_3$ in the second organic solvent, is first heated in the reaction zone to a reflux temperature, for example, at a temperature greater than about 90° C., preferably greater than about 95° C., but typically lower than about 110° C. At such a high reflux temperature, the condensation reaction is fast and the reflux drives off HCl quickly from the solution phase, so that the HCl evolution rate is controlled by the rate of feed solution addition. The rate of HCl evolution advantageously is controlled to be within the capacity of the sodium hydroxide scrubber employed to avoid pressure buildup and excess heat generation in the scrubber. The feed solution is then added at a rate such that the reflux temperature is maintained substantially isothermally during the course of the addition. In this embodiment, it is noted that the feed pipes containing the feed solution do not need to be maintained at a high temperature as in the first embodiment described hereinabove. Rather, the polar aprotic organic solvent provides the necessary solubilization of the aromatic diol at ambient temperature.

In a preferred embodiment of the process, the aromatic diol is 2,2-biphenol; the first organic solvent is a mixture of tetrahydrofuran and toluene; and the second organic solvent is toluene. The feed solution is prepared by dissolving 2,2'-biphenol in a mixture of tetrahydrofuran and toluene advantageously at about ambient temperature, preferably above about 40° C., and advantageously below about 65° C., preferably below about 60° C. The feed solution comprises advantageously greater than about 10 percent, preferably greater than about 20 percent, and advantageously less than about 50 percent, preferably less than about 40 percent 2,2'-biphenol by weight, based on the weight of the feed solution. The feed solution can be either used immediately or, optionally, cooled to ambient temperature. Any weight ratio of tetrahydrofuran to toluene can be employed so long as the solvent mixture is capable of solubilizing the aromatic diol essentially completely at ambient temperature. The weight ratio of tetrahydrofuran to toluene advantageously is greater than about 1/10, preferably, greater than about 1/5, and advantageously is less than about 10/1, preferably, less than about 5/1. In the preferred embodiment, the condensation reaction advantageously is carried out in a reactor equipped with a reflux condenser, the top of which is purged with a stream of an inert gas, such as nitrogen, which then passes through a sodium hydroxide scrubber. Toluene and then $PCl_3$ are charged into the reactor advantageously at ambient temperature. The volume of toluene charged into the reactor advantageously is greater than about one time, preferably greater than about 2 times, more preferably greater than 3 times, and advantageously is less than about 15 times, preferably less than about 13 times, more preferably less than 11 times the volume of the $PCl_3$. The molar ratio of the $PCl_3$ charged into the reactor to 2,2'-biphenol in the feed solution advantageously is greater than about 1.0, preferably greater than about 1.2, and advantageously is less than about 3.5, preferably less than 3.3, more preferably less than 3.1, still more preferably less than about 2.9, still more preferably less than about 2.7, still more preferably less than about 2.5, still more preferably less than about 2.3, still more preferably less than about 2.1, and still more preferably less than about 1.9.

The condensation reaction is carried out by first heating the toluene/$PCl_3$ solution in the reactor to a reflux at a reaction temperature above about 90° C., preferably at about 98° C., but less than about 110° C. and then adding the feed solution into the reactor in a rate such that the reflux is maintained during the addition of the feed solution and the reaction temperature remains substantially isothermal, preferably at 98° C.±5° C. The addition of the feed solution to the reaction zone is typically effected in more than about 3 hours, preferably more than about 4 hours, more preferably, more than about 5 hours, and advantageously in less than about 60 hours, preferably in less than about 55 hours, and more preferably in less than about 50 hours. As in other embodiments described herein, the condensation reaction is fast and the reflux drives off HCl quickly so that the HCl evolution rate is controlled by the rate of feed solution addition. Moreover, the rate of HCl evolution advantageously is controlled to be within the capacity of the sodium hydroxide scrubber. Such a reaction condition is preferred because it reduces the concentration of HCl in the solution phase and consequently minimizes reaction of HCl with tetrahydrofuran.

In the absence of a nitrogen base, the yield of the phosphoromonochloridite varies from about 70 mole percent to about 98 mole percent, based on the moles of aromatic diol employed in the process. The variation in yield depends on levels of trace unidentified impurities in the aromatic diol, which levels of unidentified impurities vary depending upon the source and/or specific batches of aromatic diol. It is desirable to be able to obtain phosphoromonochloridite yields consistently in the high end of the yield range. Surprisingly, a consistently high yield of phosphoromonochloridite has been achieved by carrying out the condensation reaction in the presence of a trace amount of a base, preferably a nitrogen base. Therefore, the process advantageously uses a trace amount of a base, preferably a nitrogen base. The trace amount of nitrogen base advantageously is less than 5 mole percent, preferably less than about 3 mole percent, but typically greater than about 0.01 mole percent, based on the moles of the aromatic diol used in the process. Non-limiting examples of nitrogen bases are pyridine, trialkylamine, and N,N-dialkylaniline. When the trace amount of base is employed, the yield of phosphoromonochloridite advantageously is greater than about 85 mole percent, preferably greater than about 90 mole percent, and more preferably greater than about 95 mole percent, based on the moles of aromatic diol employed in the process.

Although the nitrogen base is capable of neutralizing HCl, the nitrogen base is not intended for neutralizing the HCl produced in the condensation reaction, because the trace amount of base used is less than 2.5 mole percent of the total moles of HCl being produced. In contrast in prior art processes, when a nitrogen base is used to neutralize HCl in phosphoromonochloridite synthesis processes as, for example, in U.S. Pat. Nos. 5,235,113; 6,031,120; and 7,196,230, U.S. patent application publication 2007/0112219 A1, and *Journal of Molecular Catalysis* A: Chemical 164 (2000) 125-130, the nitrogen base is generally used in greater than one molar equivalent per molar equivalent of HCl produced.

The phosphoromonochloridite produced in each embodiment of the process advantageously is isolated as a solution of one or more of the aforementioned organic solvents by removing excess $PCl_3$ either by evaporation under reduced pressures or by distillation under either atmospheric pressure or reduced pressures. Some of the organic solvent(s) may be removed before, with, or after removal of the excess PCl$_3$. For example, in the preferred embodiment, 1,1'-biphenyl-2,2'-diyl phosphoromonochloridite advantageously is isolated as a toluene solution by distilling excess PCl$_3$ and tetrahydrofuran from the reaction product solution. A neat phosphoromonochloridite product can be obtained by distillation, if desired. The isolated yield of the phosphoromonochloridite advantageously is greater than about 85 mole percent, preferably greater than about 90 mole percent, and more preferably greater than about 95 mole percent, based on the moles of aromatic diol employed.

The excess, unconverted amount of PCl$_3$ recovered from the reaction solution advantageously can be recycled to the process. If the excess amount of PCl$_3$ is recovered as a mixture comprising a polar aprotic organic solvent, such as tetrahydrofuran, which is used as the first organic solvent or a component thereof, the polar aprotic organic solvent preferably is removed from the mixture before the recovered PCl$_3$ is reused.

The phosphoromonochloridite isolated from the process, as described hereinabove, can be used without further purification for preparing organopolyphosphites by condensing the phosphoromonochloridite with an organic poly-hydroxy compound. The phosphoromonochloridite can be used either as a solution of one or more of the aforementioned organic solvents or in neat form in the subsequent organopolyphosphite synthesis. Any impurities and/or trace amount of HCl-nitrogen base salt carried over from the phosphoromonochloridite synthesis solution can be eliminated during isolation of the organopolyphosphites. Procedures for preparing and isolating organopolyphosphites are well known in the art; see for example, U.S. Pat. Nos. 6,031,120; 5,663,369; and 4,769,498.

The process of this invention, described hereinabove, of preparing a phosphoromonochloridite has one or more of the following advantages, including: a) employing a feed solution of the aromatic diol to control the reaction rate-thereby resulting in higher phosphoromonochloridite yield and less by-products; b) using a lower molar ratio of PCl$_3$ to the aromatic diol used-thereby reducing excess amount of PCl$_3$; and c) producing only a trace amount of nitrogen base-HCl salt-thereby reducing cost.

Specific Embodiments of the Invention

The following examples are illustrative of the present invention and are not to be regarded as limiting thereof. Variations in reaction conditions, such as reactants, temperatures and solvents, will be apparent to those skilled in the art, based on the description and examples contained herein. All parts, percentages, and proportions referred to herein are given by weight, unless otherwise indicated.

Example 1

Preparation of 1,1'-Biphenyl-2,2'-Diyl Phosphoromonochloridite in the Presence of Trace Amount of Pyridine 2.2'-Biphenol (283 kilogram (kg), 1521 moles) is dissolved in 508 kg tetrahydrofuran, 151 kg toluene and 3.2 kg pyridine (4.0 moles) by heating to about 50° C. and then cooling to ambient temperature (20-25° C.) to make a feed solution. The feed solution is then added over a period of 24 hours to a stirred and refluxed solution of PCl$_3$ (318 kg, 2317 moles) in toluene (1636 kg) at an addition rate sufficient to maintain a reaction temperature of 98° C. The stirring is continued until greater than 98 percent of the 2,2'-biphenol is reacted as determined by taking aliquots for $^{31}$P NMR. The additional reaction time is about 2 hours. The $^{31}$P NMR spectrum shows that the yield of 1,1'-biphenyl-2,2'-diyl phosphoromonochloridite is 97 mole percent, based on moles of 2,2'-biphenol employed, with reminder being by-products. The excess PCl$_3$ and tetrahydrofuran are removed by distillation at atmospheric pressure. The resulting toluene solution containing the product 1,1'-biphenyl-2,2'-diyl phosphoromonochloridite is used without further purification in subsequent bisphosphite preparations.

Comparative Experiment 1

Preparation of 1,1'-Biphenyl-2,2'-Diyl Phosphoromonochloridite without any Added Base Example 1 is repeated, with the exception that no pyridine base is used. Moreover, this comparative example is carried out using 2,2'-biphenol from the same batch that is used in Example 1. Amounts of reagents and reaction conditions are essentially identical to those used in Example 1. The $^{31}$P NMR spectrum shows that the yield of 1,1'-biphenyl-2,2'-diyl phosphoromonochloridite is 85 mole percent, based on moles of 2,2'-biphenol employed, with reminder being by-products. When Comparative Experiment 1 is compared with Example 1, it is seen that the small quantity of base used in the example of the invention increases the yield of phosphoromonochloridite to 97 mole percent, as compared with 85 mole percent when no base is employed. The comparison is made under controlled process conditions using an aromatic diol taken from the same batch source.

What is claimed is:
1. A process for preparing a phosphoromonochloridite comprising,
contacting an aromatic diol represented by the following formula:

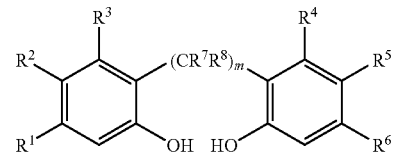

wherein:
m is zero, 1, or 2;
$R^1$, $R^2$, $R^3$, $R^4$, $R^5$, $R^6$, $R^7$ and $R^8$ are each independently selected from hydrogen, halogen, and $C_1$-$C_{10}$ substituted or unsubstituted hydrocarbyl moieties;
optionally, $R^2$ can be bonded to $R^3$ to form a substituted or unsubstituted hydrocarbylene moiety so as to form a 5- or 6-membered ring; and/or
optionally, $R^4$ can be bonded to $R^5$ to form a substituted or unsubstituted hydrocarbylene moiety so as to form a 5- or 6-membered ring;
with phosphorus trichloride (PCl$_3$) in a reaction solution in a reaction zone, which solution comprises greater than about 0.01 to less than 5 mole percent of a nitrogen base, calculated on moles of aromatic diol used, at a reaction temperature sufficient to produce the phosphoromonochloridite represented by the following formula:

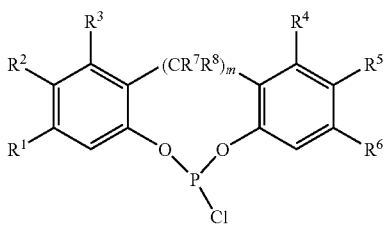

wherein m and $R^1$ through $R^8$ have the definitions given hereinabove, and sufficient to drive off HCl being produced from the reaction solution; wherein the contacting is carried out by adding a feed solution of the aromatic diol to the reaction zone comprising $PCl_3$ to form the reaction solution, the addition being at such a rate that the reaction temperature remains substantially isothermal, the feed solution comprising essentially all of the aromatic diol dissolved in a first organic solvent, and wherein the molar ratio of $PCl_3$ to aromatic diol dissolved in the reaction solution at any given time is greater than 10:1.

2. The process of claim 1 wherein m is zero or 1.

3. The process of claim 1 wherein $R^1$, $R^6$, $R^7$ and $R^8$ are each hydrogen.

4. The process of claim 1 wherein the aromatic diol is 2,2'-biphenol.

5. The process of claim 1 wherein the first organic solvent is a hydrocarbon or chlorinated hydrocarbon compound having a boiling point of greater than about 90° C. and less than about 250° C.

6. The process of claim 1 wherein the first organic solvent is a polar aprotic organic solvent having a dielectric constant greater than about 6.

7. The process of claim 1 wherein the first organic solvent is a mixture of a polar aprotic organic solvent having a dielectric constant greater than about 6 and a hydrocarbon or chlorinated hydrocarbon compound having a boiling point greater than about 90° C. and less than about 250° C.

8. The process of claim 7 wherein the polar organic solvent is tetrahydrofuran.

9. The process of claim 1 wherein the reaction zone further comprises a second organic solvent in a volume from about one time to about 15 times of the volume of $PCl_3$.

10. The process of claim 9 wherein the second organic solvent is a hydrocarbon or chlorinated hydrocarbon compound having a boiling point of greater than about 90° C. and less than about 250° C.

11. The process of claim 5 wherein the hydrocarbon or chlorinated hydrocarbon compound is selected from the group consisting of toluene, chlorobenzene, o-xylene, m-xylene, p-xylene, ethylbenzene, heptane, octane, and mixtures thereof.

12. The process of claim 1 wherein the feed solution comprises from greater than about 5 percent to less than about 50 percent of the aromatic diol by weight, based on the weight of the feed solution.

13. The process of claim 1 wherein the molar ratio of the $PCl_3$ to total moles of aromatic diol employed is greater than about 1.0 to less than 3.5.

14. The process of claim 1 wherein the contacting is conducted at a reaction temperature greater than about 40° to below about 115° C.

15. The process of claim 14 wherein the feed solution is added into the reaction zone in a time greater than about 3 hours to less than about 60 hours.

16. The process of claim 1 wherein the process further comprises removing unreacted $PCl_3$ to obtain a solution of the phosphoromonochloridite.

17. A process of preparing 1,1'-biphenyl-2,2'-diyl phosphoromonochloridite, the process comprising, contacting 2,2'-biphenol with $PCl_3$ in a reaction solution in a reaction zone, which reaction solution comprises greater than about 0.01 and less than 5 mole percent of a nitrogen base, calculated on moles of the 2,2'-biphenol, at a temperature sufficient to produce 1,1'-biphenyl-2,2'-diyl phosphoromonochloridite and sufficient to reflux the reaction solution to drive off hydrogen chloride produced as a co-product; wherein the contacting is carried out by adding a feed solution comprising the 2,2'-biphenol essentially all dissolved in a mixture of tetrahydrofuran and toluene into the reaction zone comprising $PCl_3$ diluted in toluene to form the reaction solution, the addition being at such a rate that the reaction temperature remains substantially isothermal.

18. The process of claim 17 wherein the molar ratio of $PCl_3$ to total 2,2'-biphenol employed is greater than about 1.0 to less than 3.5.

19. The process of claim 17 wherein the reaction temperature is about 98° C.±5° C. and the addition of the feed solution takes from more than about 3 hours to less than about 60 hours.

20. The process of claim 17 wherein the weight ratio of tetrahydrofuran to toluene is greater than about 1/10 and less than about 10/1.

* * * * *